(12) United States Patent
Hirsch

(10) Patent No.: US 7,108,872 B1
(45) Date of Patent: Sep. 19, 2006

(54) USE OF ODORANTS TO ALTER BLOOD FLOW TO THE VAGINA, AND ARTICLE OF MANUFACTURE THEREOF

(75) Inventor: Alan R. Hirsch, Riverwoods, IL (US)

(73) Assignee: Inscentivation, Inc., Chicago, IL (US)

( * ) Notice: Subject to any disclaimer, the term of this patent is extended or adjusted under 35 U.S.C. 154(b) by 684 days.

(21) Appl. No.: 09/707,655

(22) Filed: Nov. 7, 2000

Related U.S. Application Data

(62) Division of application No. 09/211,507, filed on Dec. 14, 1998.

(60) Provisional application No. 60/069,460, filed on Dec. 15, 1997.

(51) Int. Cl.
*A61K 35/78* (2006.01)
*A61F 13/00* (2006.01)

(52) U.S. Cl. ............. 424/758; 424/725; 424/757; 424/434; 424/489

(58) Field of Classification Search ......... 424/725, 424/758, 434, 489; 514/929
See application file for complete search history.

(56) References Cited

U.S. PATENT DOCUMENTS

| | | | |
|---|---|---|---|
| 3,948,257 A | | 4/1976 | Bossak |
| 4,285,468 A | * | 8/1981 | Hyman |
| 4,493,869 A | * | 1/1985 | Sweeny et al. |
| 4,671,959 A | | 6/1987 | Warren et al. |
| 4,735,358 A | | 4/1988 | Morita et al. ............ 239/1 |
| 5,137,869 A | * | 8/1992 | Sprecker et al. |
| 5,155,045 A | | 10/1992 | Cutler et al. ............ 436/65 |
| 5,382,567 A | | 1/1995 | Fuwa et al. |
| 5,419,879 A | | 5/1995 | Vlahakis et al. |
| 5,575,992 A | * | 11/1996 | Kunze |
| 5,759,521 A | | 6/1998 | Hirsch |
| 5,770,206 A | * | 6/1998 | Nicolicchia |
| 5,885,614 A | | 3/1999 | Hirsch |
| 5,904,916 A | * | 5/1999 | Hirsch ............ 424/45 |
| 6,106,837 A | | 8/2000 | Hirsch |

FOREIGN PATENT DOCUMENTS

| | | |
|---|---|---|
| DE | 2618614 | 11/1977 |
| DE | 29709473 | 9/1997 |
| GB | 569740 | 6/1945 |

OTHER PUBLICATIONS

International Product Allert bulletin entitled "Poan Washable Cold Cream". Jun. 1, 1994. PROMT Abstract.*
McMath, R. "The Skin Trade Goes Natural". Adweek's Marketing Week. Aug. 27, 1990. PROMT Abstract.*
The Drug & Cosmetic Industry publication entitled "Scentual responses". Jan. 1996. Text—2 pp. PROMT database.*
H. Sugano, "Effects of Odors on Mental Function" (abstract), *JASTS* 22 (1988): 303.
A.R. Hirsch and L.H. Johnson, "Odors and Learning," *Journal of Neurological and Orthopedic Medical Surgery* 17 (1996): 119-26.
H. Ellis, *Sexual Selection in Man* (F.A. Davis Co., 1906), 65.
W. Velle, "Sex Differences in Sensory Functions," *Perspectives in Biology and Medicine* 30, No. 4 (summer 1987): 491-522.
R.H. Porter et al., "Recognition of Kin through Characteristic Body Odors," *Chemical Senses* 11, No. 3 (1986): 389-95.
R.L. Doty et al., "Sex Differences in Odor Identification Ability: A Crosscultural Analysis," *Neurophysiologia* 23 (1985): 667-72.
M.N. McClintock "Menstrual Synchorny and Suppression," *Nature* 299 (1971): 244-45.
C.A. Graham and W.C. McGrew, "Menstrual Synchrony in Female Undergraduates Living on a Coeducational Campus," *Psychoneuroendocrinology* 5 (1980): 245-52.
F.J. Kallmann et al., "The genetic aspects of primary eunuchoidism," *Am. J. Mental Deficiency* 48: 203-236 (1944).
A.R. Hirsch et al., *Chemical Senses* (Abstracts 124-128) 17 (5): 642-3 (1992).
R.R. Gustavson et al., M.E. Dawson, and D.G. Bonnett, "Androstenol, a Putative Human Pheromone, Affects Human (*Homo sapiens*) Male Choice Performance," *Journal of Comparative Psychology* 101 (1987): 210-12.
M. Kirt-Smith et al., "Human Social Attitudes Affected by Androstenol," *Research Communication in Psychological Psychiatry and Behavior* 3 (1978): 379-84.
N.M. Griffiths and R.L.S. Patterson, "Human Olfactory Responses to 5 a-androst-16-en-3-one- Principal Component of Boar Taint," *J. Agric. Fd. Chem.* 21 (1970): 4-6.
N.M. Morris and J.R. Urdry, "Pheromonal Influences on Human Sexual Behavior: An Experimental Search," *Journal of Biological Science* 10 (1978): 147-57.
K. Larsson, "Impaired Mating Performances in Male Rats after Induced Anosmia Peripherally or Centrally," *Brain, Behavior, and Evolution* 4 (1971): 463-71.

(Continued)

*Primary Examiner*—Christopher R. Tate
(74) *Attorney, Agent, or Firm*—Whyte Hirschboeck Dudek SC

(57) ABSTRACT

A non-invasive method of altering vaginal blood flow in a female individual to augment or lessen sexual arousal is provided. The method involves administering an individual odorant or odorant mixture for inhalation that is sufficient to alter vaginal blood flow of the female by about −20% to about +30% compared to a baseline vaginal blood flow without inhalation of the odorant. Also provided is a method for screening an odorant for its capacity to increase or decrease vaginal blood flow, and an article of manufacture, or kit, containing an odorant and instructions for its use in altering vaginal blood flow.

14 Claims, No Drawings

OTHER PUBLICATIONS

R.L. Doty et al., "Endocrine, Cardiovascular, and Psychological Correlates of Olfactory Sensitivity Changes during the Human Menstrual Cycle," *Journal of Comparative Physiological Psychology* 95 (1981): 45-60.

R.H. Porter and J.D. Moore, "Human Kin Recognition by Olfactory Cues," *Physio. Behavior* 21 (1981): 493-95.

R.H. Porter et al., "Maternal Recognition of Neonates through Olfactory Cues," *Physio Behavior* 30 (1983): 151-54.

T. Lord and M. Kasprazak, "Identification of Self through Olfaction," *Perceptual and Motor Skills* 69 (1989): 219-24.

M.J. Russell, T. Mendelson, and H.V.S. Peeke, "Mothers' Identification of Their Infants' Odors," (1982, in preparation).

W.S. Cain, "Odor Identification by Males and Females: Predictions vs. Performance," *Chemical Senses* (1982): 129-42.

R.L. Doty et al., "Communication of Gender from Human Axillary Odors: Relationship to Perceived Intensity and Hedonicity," *Behavioral Biology* 23 (1978): 373-80.

A.R. Hirsch and G.S. Bussell, "The Effects of Inebriation on Olfaction," *Journal of Investigative Medicine* 43 (Sep. 1995): 422A.

R.L. Moss, "Modification of Copulatory Behavior in the Female Rat Following Olfactory Bulb Removal," *Journal of Comparative and Physiological Psychology* 74 (1971): 374-82.

A.R. Hirsch, "Olfaction and Anxiety," *The Clinical Psychiatry Quarterly* 16, No. 1 (1993): 4.

H. Sugano, "Effects of Odors on Mental Function" (abstract), *Japanese Association for the Study of Taste and Smell* 22 (1988): 2.

P.D. Maclean and D.W. Ploog, "Cerebral Representation of Penile Erection," *Journal of Neurophysiology* 25 (1962): 29-55.

R.C. Kolodny, W.H. Masters, and V.E. Johnson, *Textbook of Sexual Medicine* (Boston: Little, Brown and Company, 1979): 321-51.

A.R. Hirsch, "Odors and the Perception of Room Size," presented at 148th Annual Meeting of the American Psychiatric Association, Miami, 1995.

A.R. Hirsch and C. Kang, "The Effects of Green Apple Fragrance on Migraine Headache," *Headache* 37, No. 5 (1997): 312.

A.R. Hirsch and T.J. Trannel, "Chemosensory Dysfunction and Psychiatric Diagnoses," *Journal of Neurological and Orthopedic Medical Surgery* 17 (1996): 25-30.

J.R. King, "Anxiety Reduction Using Fragrances," in *Psychology and Biology of Fragrance* (London: Chapman and Hall, 1988), 147-65.

D.L. Chambles et al., "Self-reported Sexual Anxiety and Arousal: The Expanded Sexual Arousability Inventory," *J. Sex. Research* 20: 241-254 (1984).

J.F. Gent et al., "Taste and Smell Measurements in a Clinical Setting," in *Clinical Measurement of Taste and Smell*, pp. 107-166, H.L. Meiselman et al., (eds.), 602 pp., MacMillan, NY (1986).

R.L. Doty et al., "The Olfactory and Cognitive Deficits of Parkinson's Disease: Evidence for Independence," *Annals Neurology* 25 (2): 166-171 (1989).

R.L. Doty et al., "The Smell Identification Test™ Administrative Manual," *Philadelphia Sensorics, Inc.*, 22 pages (1983).

E. Frank, C. Anderson, and D. Rubenstein, "Frequency of Sexual Dysfunction in 'Normal' Couples," *New England Journal of Medicine* 299 (Jul. 20, 1978): 111.

J. Durden-Smith and D. DeSimone, *Sex and the Brain* (New York: Arbor House, 1983), 215.

M.D. Kirk-Smith, S. Van Toller, and G.H. Dodd, "Unconscious Odour Conditioning in Human Subjects," *Biological Psychology* 17 (1983): 221-31.

J.J. Geer, P. Morokoff, and P. Greenwood, "Sexual Arousal in Women: The Development of a Measurement Device for Vaginal Blood Volume," *Archives of Sexual Behavior* 3 (1974): 559-64.

W. Hamilton and P. Arrowood, "Copulatory Vocalizations of the Chacma Baboons, Gibbons, and Humans," *Science* 200, No. 4348 (Jun. 23, 1978): 1405-9.

E.F. Hoon et al., "The SAI: An Inventory for the Measurement of Female Sexual Arousability," *Arch. Sex Behav.* 5:291-300 (1976).

G. Buchbauer, *Z. Naturfursch Sect C Biosci.* 46 (11-12):1,067-1,072, (1991).

T. Komori, *Neuroimmunomodulation*, 2:(3):174-180, (1995).

Yankee Candle Co. website —http://www.yankeecandle.com, product information, 3 pp., downloaded from web Sep. 2004.

* cited by examiner

USE OF ODORANTS TO ALTER BLOOD FLOW TO THE VAGINA, AND ARTICLE OF MANUFACTURE THEREOF

CROSS-REFERENCE TO RELATED APPLICATIONS

This application is a divisional of U.S. patent application Ser. No. 09/211,507, filed Dec. 14, 1998, and claims the benefit of U.S. Provisional Application Ser. No. 60/069,460, filed Dec. 15, 1997.

BACKGROUND OF THE INVENTION

Various researchers have focused attention on odors and their connection with sexuality. Almost a hundred years ago, Sigmund Freud was concerned that if the sense of smell was not repressed, men—but not necessarily women—would walk around sexually excited all the time. Freud also linked odor with the Oedipal conflict when he said that during a boy's development, he learns to recognize the odor of both parents, and eventually he comes to dislike the father's odors and have positive associations with the mother's odors. Although Freud also spoke of the Electra Complex, a corresponding development conflict in girls, he made no mention of the significance of the parent's odors in female psychological maturation.

In men, an erection occurs when increased blood flow to the penis causes spongelike chambers to become engorged as the blood vessels of the penis expand. In women, arousal causes increased blood flow to the vagina, which expands the vaginal tissues and stimulates the release of lubricating fluids along the walls of the vagina. The clitoris becomes engorged during the arousal phase because of increased blood flow to the region.

Sexual dissatisfaction is common among married couples in our society, and arousal disorders are a very common form of sexual dysfunction. In the early 1950s, a survey by sex researcher Alfred Kinsey found that 10 percent of married women never experienced coital orgasm. (Kinsey et al., *Sexual Behavior in the Human Female*, Philadelphia: W.B. Saunders (1953)). In 1956, a British study of 3,705 women reported that 10 percent of women rarely experienced orgasm and another 5 percent never experienced orgasm during intercourse. (E. Chesser, *The Sexual Marital and Family Relationships of the English Woman*, London: Hutchinson's Medical Publications (1956)). In the 1970s, a study in the United States reported 17 percent of women seen at a gynecologic clinic stated that they had difficulty achieving orgasm with a partner, and 6 percent had never experienced orgasm with a partner. (E. Frank et al., *N. Engl. J. Medicine* 299:111 (Jul. 20, 1978)).

Research into olfactory-related sexual behavior has been documented in laboratory animals. Pheromones, which are chemical substances produced by an organism for purposes of chemo-communication with another of the same species, have been documented in many animals. Pheromones are not consciously recognized by the brain but influence hormone production, and sexual attraction, drive and even behavior. Although pheromones exist throughout the animal kingdom, it is not known for certain that human pheromones exist. One postulated human pheromone system concerns menstruation. It has been observed that women who live in close contact with one another menstruate together. Another system involves the steroid androsterone which has been named as a pheromone that is secreted from the apocrine glands located in the underarm area and around the genital organs. Androsterone has been found to have an attractant effect on women and an aversive effect on men. Alternate theories suggest that what we call potential pheromones are simply odors associated with sex, and human response to them is conditioned.

There has been other research into the olfactory-sexual link. When the olfactory bulb was lesioned in hamsters, it caused an impaired sex drive. An olfactory-sexual connection has also been observed in laboratory animals that were castrated. The castration led to both impaired sexual drive and olfactory functioning. Ovariectomies led to both impaired sexual functioning and reduced olfactory ability. Lesions of the olfactory bulb or of the nasal cartilage alone, caused both an olfactory deficit and a malformation of the developing animal's sex organs. These studies indicate a link between olfaction, olfactory organs and sexual functioning.

The linkage between olfactory function and sexual function has also been recognized in a clinical setting. Over 17% of individuals with chemosensory dysfunction who develop impaired sexual desire or other sexual dysfunction, (i.e., Kallmann's syndrome), have both an olfactory deficit and impaired sexual drive and functioning. (Kallmann, F. J., Schoefeld, W. A., and Barrera, S. E., "The genetic aspects of primary eunuchoidism," *Am. J. Mental Deficiency* 48:203–236 (1944)). Other diseases that impair both olfactory ability and sexual functioning concomitantly include cerebral vascular disorders, Parkinson's disease, senile dementia of the Alzheimer's type, hypothyroidism, and vitamin deficiency states including B12 deficiency.

Treatment of a repressed or overly stimulated sex drive can include counseling directed toward dealing with insecurities and enhancing feelings of affection and receptiveness, or reducing sexual aggressiveness. Treatments for enhancing or inhibiting female sexual capacity and response include medications such as vaginal lubricants, or psychotherapy, group therapy, cognitive therapy or behavior therapy. However, such treatments have not been totally effective, are invasive can cause unwanted side effects, and are inconvenient and complex.

Therefore, an object of the invention is to provide a non-invasive method of enhancing or inhibiting the female sexual response and arousal level, that is convenient, safe, and easy to perform.

SUMMARY OF THE INVENTION

These and other objects are achieved in a non-invasive method of altering vaginal blood flow in a female individual to augment or lessen sexual arousal. The method involves administering an amount of an odorant or odorant mixture for inhalation that is sufficient to alter vaginal blood flow of the female by about −20% to about +30% compared to blood flow without being given the odorant. Also provided is a method for screening an odorant for its effect in increasing or decreasing vaginal blood flow, and a kit, or article of manufacture, containing a odorant and instructions for its use in altering vaginal blood flow.

DETAILED DESCRIPTION OF THE INVENTION

In one embodiment of the invention, the odorant can be administered in an amount sufficient to increase vaginal blood flow of the female individual. By increasing vaginal blood flow, the female individual will experience increased or enhanced sexual arousal. Examples of odorants and odorant mixture that can be administered to increase vaginal blood flow by about 10–30%, include a baby powder odorant, a mixture of licorice-based odorant and banana nut bread odorant, a mixture of a licorice-based odorant and cucumber odorant, a floral-aldehydic perfume fragrance such as Chanel No. 5 and White Linen, a mixture of lavender and pumpkin pie odorants, and a mixture of baby powder and chocolate odorants. Examples of licorice-based odorants include a black licorice odorant, and Good N' Plenty® (licorice and anise) odorant. Such odorants are commercially available, for example, from International Flavors and Fragrances, Inc. (IFF, New York, N.Y.), Energy Essentials, AromaTech, Inc. (Somerville, N.J.), Florasynth, Inc. (Teterboro, N.J.), and as essential oils. Such individual odorants and odorant mixtures have been found to be particularly useful in increasing vaginal blood flow in female individuals who are highly aroused by masturbation.

According to the invention, odorants can also be administered to decrease vaginal blood flow of a female individual. With a reduction in vaginal blood flow, the female individual experiences an inhibited or reduced level of sexual arousal. Examples of odorants and odorant mixture that can be administered to decrease vaginal blood flow by about 10–20% include a licorice-based odorant alone, a mixture of a licorice-based odorant and cucumber odorant, a cologne such as Old Spice®, a floral-aldehydic perfume fragrance such as Chanel No. 5 and White Linen, a charcoal barbecue meat odorant, and a cherry odorant. Such odorants and odorant mixtures have been found to be particularly useful in reducing vaginal blood flow in female individuals who are minimally or not highly sexually aroused by masturbation or manual manipulation of the female genitals.

In the use of odorants to stimulate or decrease vaginal flow, it is preferred that the subject individual is presented with the odorant at a suprathreshold concentration (e.g., about 25–55 decismel units), but not irritative level, and inhales the odorant for about 1–3 minutes.

An odorant is presented at a suprathreshold level when the decismel level or concentration of the odorant is beyond that needed to be detected by a normosmic individual. At its irritative level, the odorant quantity is so high and intense that the odorant stimulates predominantly the trigeminal nerve (for pain) rather than the olfactory nerve and, hence, is perceived as noxious or painful. The irritation threshold of the patient is the lowest concentration of the substance that causes immediate stinging or burning sensations in the nose, or stinging or lacrimation of the eye. See, J. F. Gent, in *Clinical Measurement of Taste and Smell*, pages 107–166, H. L. Meiselman et al. (eds.), 602 pp., MacMillan, NY (1986); R. L. Doty et al., *Ann. Neurol.* 25: 166–171 (1989); E. Koss et al., *Neurology* 38: 1228–1232 (1988); and R. Doty, *The Smell Identification Test: Administration Manual* 1983: 13–14, Philadelphia: Sensonics, Inc. (1983).

Preferably, prior to the administration of the odorant, the individual undergoes olfactory testing according to a test such as the University of Pennsylvania Smell Identification Test (UPSIT), a 40-question forced-choice, scratch-and-sniff identification test, and the Chicago Smell Test, a 3-item detection and identification test (R. Doty, *The Smell Identification Test: Administration Manual* 1983: 13–14, Philadelphia: Sensonics, Inc. (1983); A. R. Hirsch et al., *Chemical Senses* 18 (5): 570–571 (1993); A. R. Hirsch et al., *Chemical Senses* 17 (5): 643 (1992)). The individual can also be evaluated for olfactory capacity (e.g. loss of smell) according to an olfactory threshold test as known and used in the art. Such a test provides a precise magnitude of loss of smell and classifies the individual as normosmic, hyposmic or anosmic, which is useful in assessing the effectiveness of a particular odorant and/or the required concentration of the odorant to provide a suprathreshold level to effectively increase or decrease blood flow to the vagina. According to that test, an odorant substance such as butyl alcohol, phenyl ethyl alcohol, or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The individual is presented with the series of dilutions in ascending order, and is asked to compare each dilution step to at least one control stimulus, such as odorless propylene glycol.

Ranges of the average normal threshold for various odorant substances can be found in the art, for example, Amoore and O'Neill, "Proposal for Unifying Scale to Express Olfactory Thresholds and Odor Levels: The "Decismel Scale"," in *Proceedings of the* 1988 *Air Pollution control Association Annual Meeting*, Paper No. 78.5 (21 pp.), Air and Waste Management Association, Pittsburgh, Pa. (1988); Amoore and Haotala, "Odor as an Aid to Chemical Safety: Odor Thresholds Compared with Threshold Limit Values and Volatiles for 214 Industrial Chemicals in Air and Water Dilution," *J. Appl. Toxicology* 3 (6):272–290 (1983).

In the art, a "normosmic" individual is one who can detect the odor of a substance without irritant sensations when the odorant is presented within the range of its average normal threshold. A "hyposmic" or "microsmic" individual has reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminel nerve function, being able to detect an odorant substance by means of irritant, tingling sensations when it is present at an irritant concentration. A patient who is able to detect pyridine vapor by means of irritant, tingling sensations caused by stimulation of the trigeminel nerve, but who cannot distinguish a pyridine odor at a lower concentration without such sensation, is considered to be anosmic having no olfactory nerve sensitivity.

The odorant substance is dispensed to a subject in a form that provides a vaporous emission for inhalation. The odorant substance can be administered in a liquid or solid form contained in a capped vessel, by opening a blister pack or scratch-and-sniff odor patch containing microcapsules of the odorant, as a spray from an aerosol or non-aerosol pump-type spray device, by means of a scented cloth, as a nasal spray, as a cologne or a cream, from a pen-like dispenser containing a liquid form of the odorant, and the like. Such a pen-type dispenser can be composed of a dispenser that has a tip impregnated with the odorant; the dispenser preferably contains a liquid form of the odorant, optionally adsorbed to a wicking material. It is preferred that the odorant is provided in a portable dispenser that is easily transportable and readily accessible by a person in need of relief, for example, a blister pack, booklet of scratch-and-sniff odor patches, pen-type dispenser, and the like.

The odorant substance can be packaged as part of a kit in association with a container such as a vial, jar, pouch, bottle, cloth, aerosolizer; blister pack, and the like, that holds an effective amount, or unit dosage amount, of the odorant to increase/decrease vaginal flow when administered to a female individual; and written or other form of instructions (e.g., video or cassette tape) of the use of the odorant to alter vaginal flow. The kit can also include a substance and instructions for testing olfactory capacity for the presence and/or identity of an odorant, and/or olfactory threshold. The various parts of the kit can be packaged separately and contained within a box or other packaging material.

Odorants can be screened for their effectiveness in altering vaginal blood flow by administering the odorant by inhalation in an amount and for a time period effective to alter vaginal blood flow. The effect of an odorant and/or odorant mixture can be assessed and measured objectively by administering a test to measure initial vaginal blood flow, and then re-testing the subject after being given the odorant. The effectiveness of the odorant on the subject to increase or decrease vaginal flow can be assessed by comparing the amount of vaginal blood flow before and after inhaling the odorant.

The effect of an odorant or mixture of odorants can also be assessed subjectively by interviewing and questioning the female individual as to the effectiveness of the odorant in increasing or decreasing the level of their sexual arousal (e.g., whether they are experiencing an increase or decrease in sexual stimulation) before and after inhaling the odorant substance.

The therapeutic implications of the present method are many. Individual females can benefit by inhaling certain odorants that will enhance or decrease their sexual arousal, and hence, help treat sexual arousal disorders. The use of odorants in increasing or decreasing vaginal blood flow provides a useful therapy that is also easy to administer for those who are in need of enhanced or repressed sexual arousal. The invention will be further described by reference to the following detailed example. This example is not meant to limit the scope of the invention that has been set forth in the foregoing description. Variations within the concepts of the invention are apparent to those skilled in the art. The disclosures of the cited references throughout the application are incorporated by reference herein.

EXAMPLE

A study was conducted to assess the effect of odorants on vaginal blood flow, a measure of the level of female sexual arousal and excitation. Thirty adult pre-menopausal, peri-alivatory women volunteered for this IRB approved study. Subjects were 18–40 years old, were not on any prescription or non-prescription medication including oral contraceptives, were literate in English, non-lactating, not actively attempting pregnancy, not smoking for at least one year, consumed less than one drink of alcohol per day, not using cocaine or other illegal drug, and had no genital sexual stimulation by self or their partner for 48 hours prior to the study session. All scored normosmic on the University of Pennsylvania Smell Identification Test.

The subjects had no diseases known to induce autonomic disorders or chemosensory disorders, and were not on medications that produce chemosensory disorders.

Methods. After being positioned on the examination table, a vaginal process graphic recording device was applied. The device was a sterile monitoring gauge, a photophlethysmograph, similar in shape to a tampon, which was placed into the vagina. The monitoring device measured pulse pressure which indicates change in blood flow to the vagina. The gauge was hooked up to a computer and changes in pulse strength were recorded on a continual basis.

A three minute period was allowed for acclamation to the experimental environment or a longer duration was allowed until stable baseline measurements were obtained (which measures vaginal bloodflow). A surgical mask untreated with any added odor, was applied over the subject's mouth and nose for one (1) minute. During this time, vaginal blood flow was recorded. After the one-minute measurement was taken, the women were asked if the odor was familiar, if they could identify it, and if they liked it or disliked it. Following this, the mask was removed for a three (3) minute, no odor "washout" period during which blood flow was measured when no mask was in place. This was to eliminate the effect of the odor—positive or negative—so that blood flow returned to baseline. In a double-blind, randomized fashion in which neither the subjects nor the test administrators knew which scents were being tested at any given time during the study, ten (10) surgical masks that had been pre-impregnated with different individual odors or odor mixtures were applied in a similar fashion as in the initial blank mask and recorded to obtain in a similar fashion to the original blank mask. After this, another blank mask and recordings were obtained, with the initial and final blank mask used as markers of baseline.

Bloodflow was determined with the farral vaginal photophlethysmograph, and computer-assisted therapy device as per published protocol. All odors were FDA/GRAS approved and impregnated on molded paper 3M surgical masks at suprathreshold, non-trigeminal levels as determined by an independent panel of the Smell and Taste Treatment Research Foundation. Statistical analysis was performed independently by the University of Illinois, School of Public Health. Statistical significance was timed by P value less than or equal to 0.05. Data was analyzed using non-parametric tests of Signed Rank Test, Wilcoxin Rank Sum Test, and Spearman's Rank Correlation Coefficient. (T. Colton, *Statistics in Medicine*, Little Brown & Co., Boston, Mass. (1974); E. L. Lehmann, *Nonparametrics: Statistical Methods Based on Ranks*, Holden-Day, New York, N.Y. (1975)).

Each woman was also given a series of tests of olfactory ability. Subjects underwent standardized olfactory testing with the University of Pennsylvania Smell Identification Tests (UPSIT), a 40-question forced choice scratch-and-sniff test in which the person is given four choices for each question and that has been normalized at age and sex. For example, in one question, an odor is presented, and the individual is asked if the odor is pizza, motor oil, peanuts, or lilac. Each subject was also given an odor threshold test, the Pyridine Olfactory Threshold test, a forced-choice test during which bottles containing various concentrations of pyridine, a chemical whose odor resembles scallops. This test evaluates the concentration of the odor that must be present before it is detectable. With this group of tests, olfactory acuity could be established, and those subjects who had a normal sense of smell and those with lesser or no ability to smell.

Subjects also underwent a series of questionnaires regarding demographic data, sexual history data, sexual history and olfactory preference. These included a vaginal blood-flow study questionnaire which queried regarding use of cologne and food hedonics, as well as sexual conduct and behavior. Subjects were questioned as to favorite colognes and whether they or their sexual partner wore a perfume or cologne on a regular basis, favorite and least favorite food, number of sexual partners and encounters in the previous thirty days, sexual preference, and odors that recalled childhood.

The subjects were also questioned about orgasmic functioning, including frequency in the last thirty days and over the previous six months. Through these questions, the number of women who experienced orgasm but did so infrequently, and a group who were multiorgasmic were determined.

The subjects also completed the Sexual Arousal Ability Inventory, a standardized test of accessing ease of arousability on a negative 1 to 5 scale (Hoon, E. F., Hoon, P. W., and Wincze, J. P., The SAI: "An Inventory for the Measurement of Female Sexual Arousability," *Arch. Sex. Behav.* 5:291–300 (1976)), and the Sexual Arousal Ability Inventory which accesses a negative 1 to 5 scale degree of anxiety induced by a variety of sexual activity (Chambles, D. L., and J. L. Lifshitz, "Self-reported Sexual Anxiety and Arousal: The Expanded Sexual Arousability Inventory," *J. Sex. Research* 20:241–254 (1984)). Each activity was rated for its ability to arouse or to inhibit arousal. Participants were asked if particular activities were either very arousing (5) or adversely affected their arousal (−1). The twenty eight questions used to assess sexual behaviors were used to rate sexual anxiety. The participants were asked to rate not only what aroused them (or turned them off) but also what activities would induced feelings of anxiety—defined as extreme uneasiness or distress. The scale was reversed, meaning the −1 indicated that the activity was relaxing or calming and 5 indicated that the activity was extremely anxiety-producing. For example, circling the number 2 in response to a question meant that the activity sometimes caused anxiety or was slightly anxiety-producing. The range allowed for differences not only among individual women, but for each woman, depending on the setting.

Results. The effect of odor on vaginal blood flow was calculated based on changes from the average of the blood-flow measured while the subject was wearing the blank masks. Vaginal blood flow changes are shown in Tables I–V, below.

The sources of odorants in the Tables were as follows:
Baby powder=Internatl. Flavors and Fragrances, Inc. (IFF) (#3169-HS)
Banana nut bread=Aromatech (#256454)
Charcoal barbecue smoke=IFF (#2185-HS)
Cherry=Orchidia (# F180075)
Chocolate=Florasynth, Inc. (#A3898)
Cologne=Old Spice®
Cucumber=Aromatech (#256452)
Good N' Plenty® (licorice-based)=Aromatech (#236923)
Lavender=Energy Essentials
Perfume=Chanel No. 5
Pumpkin pie=Florasynth, Inc. Energy Essentials (#AG-6956)

Table I, below, shows the average change in vaginal blood flow of the entire group of female test subjects (n=30) when administered individual odorants and odorant mixtures.

TABLE I

AVERAGE % CHANGE IN VAGINAL BLOOD FLOW IN TOTAL GROUP OF FEMALES

| ODORANT | % CHANGE IN VAGINAL BLOOD FLOW (OVER BASELINE MEASUREMENT) |
|---|---|
| Good N' Plenty ® + cucumber | +13 % |
| Baby powder | +13% |
| Pumpkin pie + lavender | +11% |
| Baby powder + chocolate | +4% |
| Perfume | +0–1% |
| Cologne | −1% |
| Good N' Plenty ® | −12% |

TABLE I-continued

AVERAGE % CHANGE IN VAGINAL BLOOD FLOW IN TOTAL GROUP OF FEMALES

| ODORANT | % CHANGE IN VAGINAL BLOOD FLOW (OVER BASELINE MEASUREMENT) |
|---|---|
| Charcoal barbecue smoke | −14% |
| Cherry | −18% |

As a group, several smells impaired arousal. Those odors that had the greatest negative effect, meaning that the baseline blood flow measurement actually decreased, were cherry (18-percent reduction) and charcoal barbecue smoke (14-percent reduction).

Other odors had a lesser effect. Male colognes decreased vaginal flow by 1 percent, and female perfumes increased it by 1 percent. A combination of baby powder and chocolate resulted in a 4-percent increase.

Pumpkin pie and lavender increased vaginal blood flow by 11 percent. The odor that had the greatest effect to induce female sexual arousal was a combination of Good & Plenty® licorice-based odorant and cucumber which increased blood flow by 13 percent.

While the Good & Plenty® licorice-based odorant and cucumber combination was arousing to most women, difference occurred among the participants based on the kinds of sexual behavior and activities preferred. For example, the women could be subgrouped into those who found masturbation arousing and those who did not. Table II, below, shows the average change in vaginal blood flow of the subgroup of female individuals who indicated a high sexual arousal with masturbation on the questionnaire. Table III, below, shows the average change in vaginal blood flow of the subgroup of female individuals who indicated repulsion or low arousal with masturbation on the questionnaire.

TABLE II

FEMALES WITH HIGH AROUSAL WITH MASTURBATION

| ODORANT | % CHANGE IN VAGINAL BLOOD FLOW (OVER BASELINE MEASUREMENT) |
|---|---|
| Good & Plenty ® + banana nut bread | +28% |
| Good & Plenty ® + cucumber | +22% |
| Perfume | +18% |

TABLE III

FEMALES WITH INHIBITION OR LOW AROUSAL WITH MASTURBATION

| ODORANT | % CHANGE IN VAGINAL BLOOD FLOW (OVER BASELINE MEASUREMENT) |
|---|---|
| Baby powder | +16% |
| Pumpkin pie + lavender | +10% |
| Good & Plenty ® | −20% |

Among women who reported being extremely aroused by masturbation, every odor tested had an arousing effect. A Good & Plenty® licorice-based odorant and banana-nut bread combination (28-percent increase) and the Good &

Plenty® licorice-based odorant and cucumber combination (22 percent) showed the greatest effect. Popular perfumes showed an 18-percent increase in vaginal blood flow, as did baby powder, which was nearly as arousing at a 16-percent increase.

Women who did not find masturbation extremely arousing showed an increase in vaginal blood flow of 16 percent in response to baby powder and a 1-percent response to lavender and pumpkin pie.

The women could also be subgrouped into those who were extremely aroused when a lover manually stimulated here genitals and those who were not. Table IV, below, shows the average percent change in vaginal blood flow of the subgroup of female individuals who indicated that they are positively aroused sexually by partner's finger manipulation of the genitals on the questionnaire. Table V, below, shows the average percent change in vaginal blood flow of the subgroup of female individuals who indicated a low to zero to negative level of arousal by partner's finger manipulation of the genitals on the questionnaire.

TABLE IV

FEMALES WHO ARE POSITIVELY AROUSED
BY GENITAL FINGER MANIPULATION BY PARTNER

| ODORANT | % CHANGE IN VAGINAL BLOOD FLOW (OVER BASELINE MEASUREMENT) |
|---|---|
| Good N' Plenty ® + cucumber | +18% |
| Pumpkin pie + lavender | +12% |

TABLE V

FEMALES WHO ARE NEGATIVELY AROUSED
BY GENITAL FINGER MANIPULATION BY PARTNER

| ODORANT | % INCREASE IN VAGINAL BLOOD FLOW (OVER BASELINE MEASUREMENT) |
|---|---|
| Perfume | −14% |
| Cologne | −14% |
| Good N' Plenty ® + cucumber | −13% |

Women who found manual genital stimulation arousing showed a 12-percent increase in vaginal blood flow in response to pumpkin pie and lavender, and averaged an 18-percent increase with the Good & Plenty® licorice-based odorant and cucumber combination.

No odors induced sexual arousal in the women who were not extremely aroused by manual genital stimulation, whereas many odors inhibited arousal, including male colognes and perfumes, both of which decreased blood flow by 14 percent. The Good & Plenty® licorice-based odorant and cucumber combination decreased blood flow by 13 percent in that group.

There were also differences found in response to odors among women who reported being multiorgasmic during at least one-third of their sexual encounters versus those who experienced a single orgasm during their sexual encounters or reported being multiorgasmic less than one-third of the time. Among those women who were frequently multiorgasmic, the inhalation of a baby powder odorant decreased vaginal blood flow (over base line) by about 8%. By comparison, in females who were mono-orgasmic were aroused in response to a baby powder odorant with an average increase of vaginal blood flow by about 15%.

Discussion. It has presently been found that certain odors can be administered to a female individual to increase or decrease vaginal blood flow which, in turn, has an impact upon female sexual arousal in both an enhancing and/or an inhibiting way. The results show that an odorant can be administered for inhalation by a female to alter her vaginal blood flow by about −20% to about +30% compared to baseline vaginal blood flow (no odorant given). The administration of odorants provides a non-invasive method of altering vaginal blood which can result in an increase or decrease in the female individual's level of sexual arousal.

As the results indicate, an odorant can be administered to increase vaginal blood flow of a female individual and enhance sexual arousal. The results showed that the most effective odor for female arousal was a combination of food odors. While women's responses to odors are not homogeneous and women respond differently depending on their preferences of sexual activities and behaviors, the licorice-based odorant and cucumber combination was the most effective odor overall.

Individual odorants and odorant mixtures that increased vaginal blood flow by about 10–30%, included a baby powder odorant, a mixture of a licorice-based odorant and banana nut bread odorant, a mixture of a licorice-based odorant and cucumber odorant, a floral-aldehydic perfume fragrance (e.g., Chanel No. 5), a mixture of lavender and pumpkin pie odorants, and a mixture of baby powder and chocolate odorants. These individual odorants and odorant mixtures were particularly effective in increasing vaginal blood flow in those female individuals who are positively sexually aroused with masturbation or by manual manipulation of the genitals.

Odorants can also be administered to decrease vaginal blood flow of a female individual and the level of sexual arousal. The odorants and odorant mixtures that caused a decrease in vaginal blood flow by about 10–20% included a licorice-based odorant alone, a mixture of a licorice-based odorant and cucumber odorant, a charcoal barbecue meat odorant, a cherry odorant, a men's cologne (e.g., Old Spice), and a floral-aldehydic perfume fragrance (e.g., Chanel No. 5). These odorants and odorant mixtures were particularly effective in reducing vaginal blood flow in those female individuals who were not sexually aroused with masturbation or by touching or manipulation of the genitals by a partner.

Although not intended to limit the invention to a particular theory, one way that the odorants can act on female sexual arousal is through a learned conditioned response. If the odor is one that the female associates with a past experience of being sexually aroused, the odor may induce a sexually arousing mechanism. This could be a primary conditioned response or through secondary effects, for example, by inducing a more positive mood state or relaxed state which may cause females to remove or reduce inhibitions. Positive moods and relaxed states can be achieved either directly through a conditioned response through a learned response paradigm, or through a phenomenon of olfactory evoked nostalgia whereby an odor induces a positive mood state in an individual as a result of recalling the past.

The odorants may also act to enhance female sexual arousal by acting directly on areas of the brain in a more physiological way. For example, the odors may have stimulated the reticular activating system of the brain which makes one awake and alert. In this alert state, the women may have become more aware of sensory stimuli in the environment, including sexual cues.

In addition, the odors may have acted directly on the brain to reduce anxiety. For example, in one study, people were placed in a coffinlike tube which induced a claustrophobic response. Odors were then added to the environment and their effect was evaluated. The odor of cucumber reduced anxiety and altered participant's perception of space. In a similar way, the odor of cucumber may have reduced anxiety among the women test subjects.

The odorants may also impact upon sexual arousal by inducing a state of risk taking or of generalized pleasure seeking as in seeking food or other pleasure-oriented responses. In addition, the odorants may inhibit associated cortical functioning that would induce a release of the "id" or the underlying limbic system functioning, hence allowing more primitive responses. This has been observed in decorticate animals (e.g., Kluvor-Bucy syndrome) and in humans who have developed marked cortical deficits, such as obese Down's syndrome individuals. Similar responses have been observed in individuals who became more tired, and thus become more easily induced to sexual arousal or eating. Similarly, cortical suppression with alcohol can lead to a lack of discrimination for sexual partners, which may be due to alcohol-induced inhibition of olfactory reception, similar indiscriminate mating as seen in rats.

For women for whom masturbation is extremely arousing, there are two theories about their response. In the study, a monitoring device was in place in the vagina throughout the test. The odors may have acted to change the women's focus of attention and enhanced the perception of touch. The presence or absence of one sensory modality can affect our perception of another. Many people say that they have improved perception of auditory stimuli when they are in total darkness. In the study, the sense of smell may have acted on the tactile sensations produced by the vaginal monitor. Further, since these women were easily sexually excited by touch, the odors may have had an even greater effect in combination with the tactile sensation produced by the monitoring device; their touch receptors were already conditioned to be more sensitive to tactile stimuli, and the olfactory stimulation further enhanced the perception of touch.

Alternatively, rather than odors increasing awareness of the vaginal monitoring device, the odors may have made the women less aware of the device. For some women, the monitor may have been slightly painful and the odors may have distracted them and, therefore, decreased their discomfort. Or, the odors may have acted physiologically to reduce pain. In a study of individuals who suffered from migraine headaches, the odor of green apple was shown to relieve pain; since pain inhibits sexual arousal, the odors may have acted to reduce the discomfort of the vaginal monitoring device. When there is minimal pain and discomfort, sexual arousal is enhanced.

One explanation for both the positive and negative responses that make anatomic sense is that the odors acted on the septal nucleus which is the erection center of the brain. Animal studies have shown that stimulation of the septal nucleus of the squirrel monkey results in erection, and a direct anatomic connection exists between the olfactory bulb and the septal nucleus. The odors may have acted directly on the septal nucleus to either stimulate or inhibit arousal.

The invention has been described by reference to detailed examples and methodologies. These examples are not meant to limit the scope of the invention. It should be understood that variations and modifications may be made while remaining within the spirit and scope of the invention. The disclosures of the cited references are incorporated by reference herein.

What is claimed is:

1. An article of manufacture, comprising, packaged together:
    a liquid odorant composition packaged in a container, the odorant composition comprising a mixture of odorants in a suprathreshold but not irritant concentration, said concentrations of the odorants being greater than an average normal threshold concentration of the odorants, said concentration being about 25–55 decismel units and effective to alter blood flow to the vagina when inhaled by a female individual; wherein the odorant mixture is selected from the group consisting of a mixture of licorice-based and banana nut bread odorants, a mixture of licorice-based and cucumber odorants, and a mixture of baby powder and chocolate odorants; and
    instructions for administering the odorant to alter blood flow to the vagina.

2. The article of manufacture of claim 1, wherein the odorant composition and the unit dosage amount of the odorant composition is effective to increase blood flow to the vagina of the female individual by about 10–30%.

3. The article of manufacture of claim 1, wherein the odorant composition and the unit dosage amount of the odorant composition is effective to decrease blood flow to the vagina of the female individual by about 10–20%.

4. An article of manufacture, comprising, packaged together:
    an odorant composition packaged in a container, the odorant composition comprising a mixture of odorants in a suprathreshold but not irritant concentration, said concentration of the odorants being greater than an average normal threshold concentration of the odorants, said concentration being about 25–55 decismel units and effective to alter blood flow to the vagina when inhaled by a female individual wherein the odorant mixture is selected from the group consisting of a mixture of licorice-based and banana nut bread odorants, a mixture of licorice-based and cucumber odorants, and a mixture of baby powder and chocolate odorants;
    instructions for administering the odorant to alter blood flow to the vagina; and at least one of:
        (i) a device for measuring blood flow to the vagina of the female individual;
        (ii) a device for administering a plurality of odorants for testing olfactory ability of the female individual; and
        (iii) a device for administering a series of odorants for testing olfactory threshold of the female individual.

5. The article of manufacture of claim 1, wherein the odorant composition is packaged within a delivery device selected from the group consisting of a vial, jar, pouch, can, bottle, and a blister pack.

6. The article of manufacture of claim 1, wherein the odorant composition is contained with a delivery device selected from the group consisting of a scented cloth, an aerosol spray device, a pump-type spray device, a nasal spray device, a vessel having a cap, and a blister pack.

7. The article of manufacture of claim 1, wherein the odorant composition is contained in a dispenser comprising a capped vessel having a tin impregnated with the odorant composition.

8. An article of manufacture, comprising, packaged together:
   an odorant composition contained in a dispenser comprising a capped vessel having a tip impregnated with the odorant composition;
   the odorant composition comprising a mixture of odorants in a suprathreshold but not irritant concentration effective to alter blood flow to the vagina when inhaled by a female individual; wherein the odorant mixture is selected from the group consisting of a mixture of licorice-based and banana nut bread odorants, a mixture of licorice-based and cucumber odorants, and a mixture of baby powder and chocolate odorants; and
   instructions for administering the odorant to alter blood flow to the vagina.

9. The article of manufacture of claim 8, wherein the dispenser contains the odorant composition absorbed to a wicking material.

10. An article of manufacture, comprising, packaged together:
   a liquid odorant composition packaged in a container, the odorant composition comprising a suprathreshold but not irritant concentration of a mixture of a licorice-based odorant and a cucumber odorant effective to alter blood flow to the vagina when inhaled by a female individual, said concentration of the odorants being greater than an average normal threshold concentration of the odorants at about 25–55 decismel units; and
   instructions for administering the odorant to alter blood flow to the vagina.

11. An article of manufacture, comprising, packaged together:
   an odorant composition packaged in a container, the odorant composition comprising a mixture of baby powder and chocolate odorants in a suprathreshold but not irritant concentration effective to increase blood flow to the vagina when inhaled by a female individual; and
   instructions for administering the odorant composition to increase blood flow to the vagina.

12. The article of manufacture of claim 11, wherein the odorant composition and the unit dosage amount of the odorant composition is effective to increase blood flow to the vagina of the female individual by about 10–30%.

13. An article of manufacture, comprising, packaged together:
   an odorant composition in the form of microcapsules contained in a scratch-and-sniff odor patch, the odorant composition comprising a suprathreshold but not irritant concentration of a mixture of a licorice-based odorant and a cucumber odorant effective to alter blood flow to the vagina when inhaled by a female individual, said concentration of the odorants being greater than an average normal threshold concentration of the odorants at about 25–55 decismel units; and
   instructions for administering the odorant to decrease blood flow to the vagina.

14. The article of manufacture of claim 13, wherein the odorant composition and the unit dosage amount of the odorant composition is effective to decrease blood flow to the vagina of the female individual by about 10–20%.

* * * * *